(12) United States Patent
Goossen

(10) Patent No.: US 9,002,456 B2
(45) Date of Patent: Apr. 7, 2015

(54) IMPLANT WITH ANTENNA ARRAY

(71) Applicant: Empire Technology Development LLC, Wilmington, DE (US)

(72) Inventor: Keith W Goossen, Howell, NJ (US)

(73) Assignee: Empire Technology Development LLC, Wilmington, DE (US)

( * ) Notice: Subject to any disclaimer, the term of this patent is extended or adjusted under 35 U.S.C. 154(b) by 0 days.

(21) Appl. No.: 13/785,861

(22) Filed: Mar. 5, 2013

(65) Prior Publication Data

US 2013/0218228 A1  Aug. 22, 2013

Related U.S. Application Data

(62) Division of application No. 12/577,909, filed on Oct. 13, 2009, now Pat. No. 8,417,340.

(51) Int. Cl.
| | |
|---|---|
| *A61N 1/00* | (2006.01) |
| *A61N 1/362* | (2006.01) |
| *A61N 1/37* | (2006.01) |
| *A61N 1/372* | (2006.01) |

(52) U.S. Cl.
CPC .............. *A61N 1/362* (2013.01); *A61N 1/3718* (2013.01); *A61N 1/37229* (2013.01)

(58) Field of Classification Search
CPC ........... A61N 1/37229; A61N 1/37223; A61N 1/3718; A61B 5/0031; A61B 5/7203; A61B 5/7221
USPC .................................. 607/32, 59–60
See application file for complete search history.

(56) References Cited

U.S. PATENT DOCUMENTS

| | | | |
|---|---|---|---|
| 5,626,630 A | 5/1997 | Markowitz et al. | |
| 6,778,856 B2 | 8/2004 | Connelly et al. | |
| 8,178,457 B2 | 5/2012 | De Rochemont | |
| 8,229,506 B2 | 7/2012 | Duet | |
| 2005/0079132 A1* | 4/2005 | Wang et al. | 424/1.11 |
| 2006/0034569 A1 | 2/2006 | Shih et al. | |
| 2006/0095093 A1* | 5/2006 | Bettesh et al. | 607/60 |
| 2007/0247388 A1* | 10/2007 | Asakura et al. | 343/834 |
| 2007/0288066 A1 | 12/2007 | Christman et al. | |
| 2008/0215121 A1 | 9/2008 | Bange et al. | |
| 2008/0234784 A1* | 9/2008 | Li et al. | 607/60 |
| 2009/0234407 A1 | 9/2009 | Hastings et al. | |
| 2009/0248105 A1 | 10/2009 | Keilman et al. | |
| 2010/0045480 A1 | 2/2010 | Vallapureddy et al. | |
| 2010/0149042 A1* | 6/2010 | Utsi et al. | 343/700 MS |
| 2010/0185055 A1* | 7/2010 | Robertson et al. | 600/117 |
| 2011/0087306 A1 | 4/2011 | Goossen | |

OTHER PUBLICATIONS

Zhen, Networking Issues in Medical Implant Communications, International Journal of Multimedia and Ubiquitous Engineering, Jan. 2009, vol. 4, No. 1, pp. 23-38.
Merli, Implanted Antenna for Biomedical Applications, IEEE 2008 (978-1-4244-2042-1/08), 4 pages.

(Continued)

*Primary Examiner* — Catherine Voorhees
(74) *Attorney, Agent, or Firm* — Jensen & Puntigam, PS

(57) ABSTRACT

Implant devices described herein may be adapted to communicate with other devices via an antenna array. The antenna array may be configured to minimize radiation to surrounding tissue and/or maximize signal power in a direction of device(s) with which the implant device communicates.

27 Claims, 10 Drawing Sheets

(56) References Cited

OTHER PUBLICATIONS

Panescu, wireless communication systems for implantable medical devices, IEEE Engineering in Medicine and Biology Magazine, Mar./Apr. 2008 (0739-5175/08), pp. 96-101.

Eldosoky, The role of the skin layer in the communication between the implanted sensors and the outside controller, undated, 4 pages.

Random Science Tools, Complex Dielectric Constant of Water Calculator, website: www.random-science-tools.com/electronics/water_dielectric.htm on Aug. 26, 2009, 1 page.

Zarlink Semiconductor, Medical Implantable RF Transceiver, Data Sheet, May 2007, 8 pages.

Remcom, Patch Antenna in Body—Antenna Design, website: www.remcom.com/examples/patch-antenna-in-body.html on Aug. 27, 2009, 6 pages.

Eldosoky, M. A. A., "The role of the skin layer in the communication between the implanted sensors and the outside controller," Paper presented at URSI General Assembly and Scientific Symposium, Aug. 2008, 4 pages.

Emrick, R. M. and Volakis, J. L., "On chip spatial power combining for short range millimeter-wave systems," Paper presented at Antennas and Propagation Society International Symposium, Jul. 2008, 4 pages.

* cited by examiner

US 9,002,456 B2

IMPLANT WITH ANTENNA ARRAY

CROSS-REFERENCE TO RELATED APPLICATIONS

Priority is claimed to U.S. patent application Ser. No. 12/577,909, entitled "IMPLANT WITH ANTENNA ARRAY", filed on Oct. 13, 2009, issued as U.S. Pat. No. 8,417,340 on Apr. 9, 2013, and which is incorporated by reference herein.

BACKGROUND

Unless otherwise indicated herein, the materials described in this section are not prior art to the claims in this application and are not admitted to be prior art by inclusion in this section.

The Federal communication Commission (FCC-USA) and the European Telecommunication Standards Institute (ETSI) have allocated radio frequency bandwidth for Medical Implanted Communication Service (MICS). MICS is an ultra-low power, unlicensed, mobile radio service for transmitting data in support of diagnostic or therapeutic functions associated with implanted medical devices. MICS permits individuals and medical practitioners to utilize ultra-low power medical implant devices, such as cardiac pacemakers and defibrillators, without causing interference to other users of the electromagnetic radio spectrum.

MICS signifies the rise of wirelessly communicating medical implants. Technological developments in this field will lead to a wide variety of life saving and life improving devices. While the many exciting developments and new devices are encouraging, significant challenges remain to be overcome.

BRIEF DESCRIPTION OF THE DRAWINGS

The features of the present disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings, in which:

DETAILED DESCRIPTION

Figure 1:
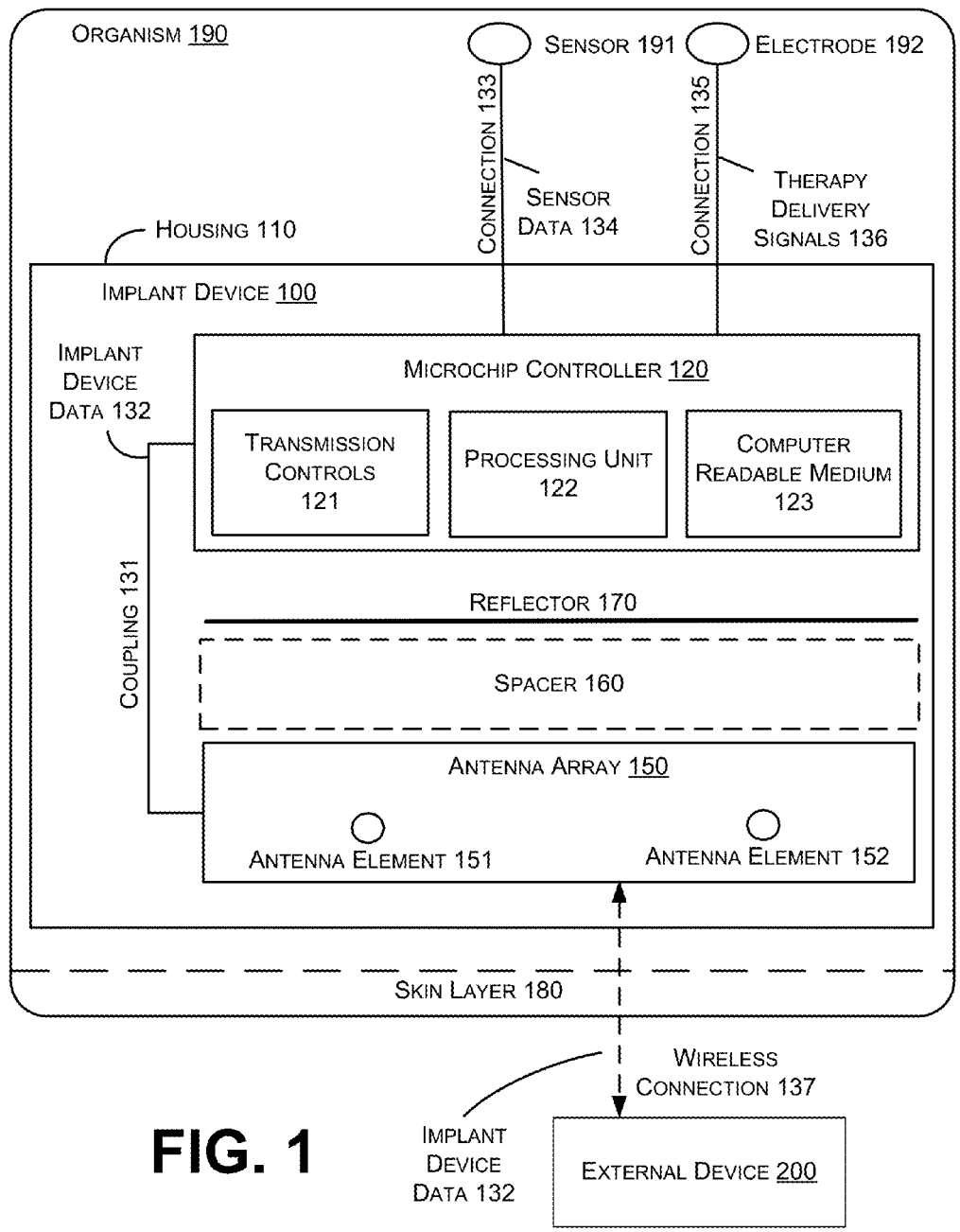
FIG. 1 is a block diagram illustrating an example implant device.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the Figures, may be arranged, substituted, combined, and designed in a wide variety of different configurations, all of which are explicitly contemplated and made part of this disclosure.

This disclosure is generally drawn, inter alia, to methods, devices, and/or systems related to implant devices. An example implant device described herein may be adapted to communicate with other devices via an antenna array. The antenna array may be configured to minimize radiation to surrounding tissue and/or maximize signal power in a direction of device(s) with which the implant device communicates.

FIG. 1 is a block diagram illustrating an example implant device 100 implanted inside an organism 190. Example implant device 100 may comprise a housing 110 in which a microchip controller 120, an antenna array 150, a spacer 160 and a reflector 170 may be disposed, along with a variety of other implant device electronics (not shown) as may be suitable for particular implant device types. Microchip controller 120 may comprise transmission controls 121, processing unit 122, and computer readable medium 123. Antenna array 150 may comprise a plurality of antenna elements 151, 152. Also illustrated in FIG. 1 are sensor 191 and electrode 192, illustrated outside the housing 110 but inside the organism 190, and external computing device 200, disposed outside the organism 190.

In FIG. 1, implant device 100 may be coupled to sensor 191 via a wired or wireless connection 133, over which sensor data 134 may be transmitted. Implant device 100 may be coupled to electrode 192 via a wired or wireless connection 135, over which therapy delivery signals 136 may be transmitted. Microchip controller 120 may be coupled to antenna array 150 via wired or wireless coupling 131, over which implant device data 132 may be transmitted. Implant device 100 may be coupled to external device 200 via a wireless connection 137, over which implant device data 132 may be transmitted.

Implant device 100 operations may be carried out by microchip controller 120, in connection with any other implant device components as suited for particular implant types. For example, where implant device 100 is a pacemaker, any currently used or future developed pacemaker components may be utilized in cooperation with, or in place of, microchip controller 120, to monitor and/or restore heartbeat rhythm according to the desired function of the particular implant type. In one example scenario, microchip controller 120 may be adapted to receive biometric data from sensor 191 in the form of sensor data 134, and may store sensor data 134 in computer readable medium 123. Microchip controller 120 may also be adapted to administer electrical energy (e.g., current, charge, voltage, etc), micro-robot control information, medications, instructions for other implant devices, or other medical services affecting the organism 190 via elements such as electrode 192. A log of implant device operations, such as a log of therapy delivery signals 136 sent to electrode 192, may also be stored in computer readable medium 123. The sensor data 134 as well as the log of therapy delivery signals 136 and a variety of other data, as discussed further herein, may generally be referred to herein as implant device data 132.

Implant device 100 may be adapted to communicate wirelessly with other devices by sending implant device data 132 via antenna array 150. For example, a pacemaker implant device 100 may from time to time wirelessly transmit stored heartbeat data via wireless connection 137 to an external device 200 configured to communicate with the pacemaker, and may also receive data and commands from the external device 200. An example external device 200 is discussed in greater detail with reference to FIG. 2. An external device 200 may for example comprise a handheld device disposed external to organism 190. Implant device data 132 may be stored, analyzed, and further transmitted by such an external device 200, as discussed in detail in connection with FIG. 10.

The antenna array 150, spacer 160 and/or reflector 170 may be configured to produce a wireless signal that may be optimized for a variety of beneficial properties. For example, in some embodiments, orientation of the housing 110 and positions and sizes of the antenna elements 151, 152, spacer 160 and/or reflector 170 may be selected to reduce electromagnetic radiation in the organism 190 and enhance signal strength for transmissions in the direction of the external device 200.

In embodiments such as FIG. 1 in which the antenna array 150 may be disposed in a fixed position inside the housing 110, the housing 110 may be designed for implantation in a predefined orientation with respect to a plane of an organism tissue layer 180. For example, the housing 110 may be designed for implantation in an orientation that places the antenna array 150 substantially parallel to the tissue layer 180 with the reflector 170 opposite the tissue layer 180. The housing 110 may for example comprise a thin wafer or coin style design which may be inserted between tissue layers.

The antenna elements 151, 152 may for example be disposed within the antenna array 150 and the oriented housing 110 such that they may also be substantially parallel to a plane of the tissue layer 180. In FIG. 1, a side view of the antenna array 150 shows cross-sections of the antenna elements 151, 152, each element comprising for example a metallic wire dipole type antenna oriented substantially perpendicular to the surface of the page, and substantially parallel to the other antenna element of the antenna array 150, and substantially parallel to the plane of the tissue layer 180. The antenna elements 151, 152 may be disposed at a fixed distance from one another, wherein the fixed distance may be selected to promote destructive interference of electromagnetic waves emitted by the individual antenna elements in the plane of the tissue layer 180, and constructive interference of the electromagnetic waves in a direction substantially normal to the plane of the tissue layer 180. In FIG. 1, the direction substantially normal to the plane of the tissue layer 180 is also the direction of the external device 200.

Furthermore, the reflector 170 may be disposed at a fixed reflecting distance from the antenna array 150, wherein the fixed reflecting distance may be selected to promote constructive interference of reflected electromagnetic waves with the electromagnetic waves being emitted by the individual antenna elements 151, 152 in a direction substantially normal to the plane of the tissue layer 180. The spacer 160 may be disposed between the reflector 170 and the antenna array 150, and the spacer 160 may be of an appropriate thickness, as discussed further in connection with FIG. 5, to promote the desired interference. The reflector 170 may thus block electromagnetic radiation that would otherwise enter the organism 190, and strengthen the signal transmitted to the external device.

In some embodiments, implant device 100 may be any electronic device implantable into an organism 190. Implant device 100 may comprise, for example, a swallowable pill-shaped device or microrobot device for administering treatment and/or gathering data which may include biometric, audio and/or video data, a device for treating hyperthermia, a pacemaker, a defibrillator, a glucose monitor, an insulin pump, a hearing aid, a device for health care facility communication, a device for medical and emergency equipment tracking, and a remote patient monitoring device. Implant device 100 may include any of the variety of technologies and components in use or as may be developed for these and other implant device types.

In some embodiments, sensor 191 and electrode 192 may be any components needed for particular implant device types. For example, different sensor types may be needed depending on the implant. In a pacemaker, a heartbeat monitor type of sensor may be used, while in a glucose monitor a glucose measurement type of sensor may be used. Sensor data 134 may comprise, for example, biometric data received at sensor 191. Biometric data may include a wide variety of data including but not limited to electrical potential data, temperature data, audio or video data, accelerometer or other motion data, and chemical environment data such as glucose measurements.

Electrode 192 may for example be replaced with an insulin pump, microrobot device controlled from implant 100, another implant in communication with implant 100, or some other device adapted for administering treatment according to the appropriate implant type, as discussed above. Therapy delivery signals 136 may comprise, for example, electrical pulses to be administered at the location of the electrode 192. Therapy delivery signals 136 may also comprise, for example, control information for the electrode 192, in embodiments in which electrode 192 is configured to receive and implement commands contained in the control information.

Given the wide variety of sensor and electrode data that may be utilized in particular implant device 100 embodiments, implant device data 132 may include any of a wide variety of data communicated between implant device 100 and another device. Devices to which implant device data 132 may be sent (e.g., transmitted) or from which implant device data 132 may be received via array 150 include, for example, sensor 191, electrode 192, other implant devices, and devices external to the organism 190. Implant device data 132 may include, for example, one or more of sensor data such as 134, therapy delivery signals such as 136, emergency alert data, implant device operations data such as operations history and scheduled operations, implant device properties data such as implant device identification, configuration, capabilities, remaining battery life, and status of various implant device components, and implant control data such as control data from an external device containing commands to be carried out by the implant device 100.

In some embodiments, the antenna elements 151, 152 of the antenna array 150 may comprise antennas of one or more antenna types. For example, antenna elements 151, 152 may comprise whip-type antennas, dipole-type antennas, planar antennas such as patch antennas and Tapered Slot Antennas (TSAs), and/or microstrip-type antennas.

In some embodiments, one or more of housing 110 orientation, antenna array 150 orientation, antenna element 151, 152 spacing, and/or reflector 170 orientation may be adjusted as appropriate to achieve a desired direction of strongest transmission. For example, by orienting the housing 110 or antenna array 150 at an angle that is not substantially parallel to the tissue layer 180, a transmission direction other than normal to layer 180 may be achieved. Similarly, antenna element spacing and/or reflector angle may be adjusted to change the direction of strongest constructive interference, to achieve angles other than normal to the tissue plane.

Figure 2:
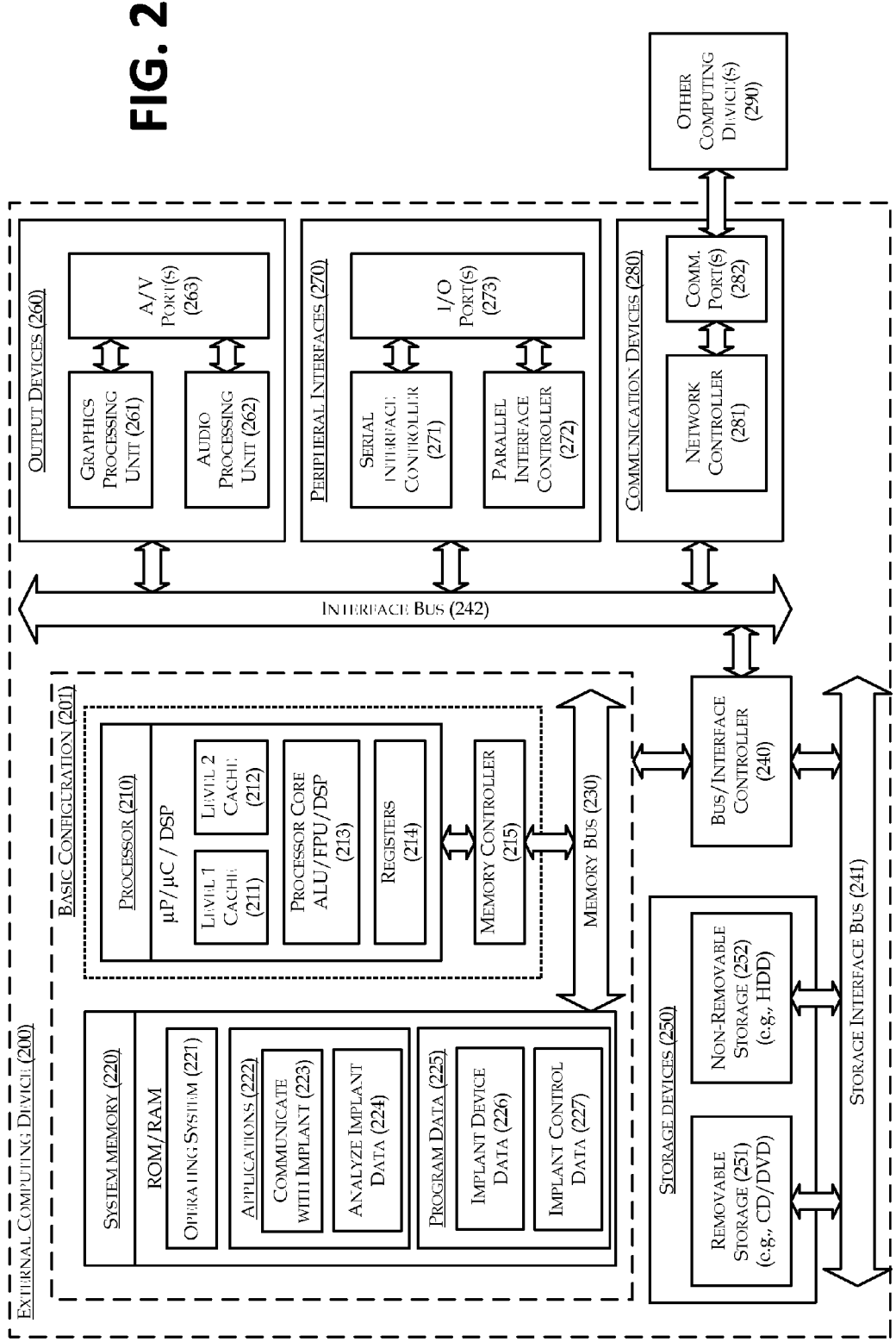
FIG. 2 is a block diagram illustrating a computing device as one example of a device with which an implant device may communicate.

FIG. 2 is a block diagram illustrating a computing device 200 as one example of a device external to the organism 190 in FIG. 1, with which an implant device 100 may communicate, arranged in accordance with at least some embodiments of the present disclosure. In a very basic configuration 201, computing device 200 typically may include one or more processors 210 and system memory 220. A memory bus 230 may be used for communicating between the processor 210 and the system memory 220.

Depending on the desired configuration, processor 210 may be of any type including but not limited to a microprocessor (µP), a microcontroller (µC), a digital signal processor (DSP), or any combination thereof. Processor 210 may include one or more levels of caching, such as a level one cache 211 and a level two cache 212, a processor core 213, and registers 214. The processor core 213 may include an arithmetic logic unit (ALU), a floating point unit (FPU), a digital signal processing core (DSP Core), or any combination thereof. A memory controller 215 may also be used with the processor 210, or in some implementations the memory controller 215 may be an internal part of the processor 210.

Depending on the desired configuration, the system memory 220 may be of any type including but not limited to volatile memory (such as RAM), non-volatile memory (such as ROM, flash memory, etc.), or any combination thereof. System memory 220 typically includes an operating system 221, one or more applications 222, and program data 225. Applications 223-224 may include, for example, communicate with implant module(s) 223 and analyze implant data module(s) 224. Program data 226-227 may include implant device data 226 and implant control data 227 that may be used by applications 223-224. Communicate with implant module(s) 223 may be customized in some embodiments for communication with implants comprising antenna arrays, such as antenna array 150 as disclosed herein. Furthermore, Communicate with implant module(s) 223 may comprise application instructions for communicating via an antenna array similar to 150 and disposed in the device 200, for two-way communication via antenna array.

Computing device 200 may have additional features or functionality, and additional interfaces to facilitate communications between the basic configuration 201 and any required devices and interfaces. For example, a bus/interface controller 240 may be used to facilitate communications between the basic configuration 201 and one or more data storage devices 250 via a storage interface bus 241. The data storage devices 250 may be removable storage devices 251, non-removable storage devices 252, or a combination thereof. Examples of removable storage and non-removable storage devices include magnetic disk devices such as flexible disk drives and hard-disk drives (HDD), optical disk drives such as compact disk (CD) drives or digital versatile disk (DVD) drives, solid state drives (SSD), and tape drives, to name a few. Example computer storage media may include volatile and nonvolatile, removable and non-removable media implemented in any method or technology for storage of information, such as computer readable instructions, data structures, program modules, or other data.

System memory 220, removable storage 251, and non-removable storage 252 are all examples of computer storage media. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium that may be used to store the desired information and that may be accessed by computing device 200. Any such computer storage media may be part of device 200.

Computing device 200 may also include an interface bus 242 for facilitating communication from various interface devices (e.g., output interfaces, peripheral interfaces, and communication interfaces) to the basic configuration 201 via the bus/interface controller 240. Example output devices 260 include a graphics processing unit 261 and an audio processing unit 262, which may be configured to communicate to various external devices such as a display or speakers via one or more AN ports 263. Example peripheral interfaces 270 include a serial interface controller 271 or a parallel interface controller 272, which may be configured to communicate through either wired or wireless connections with external devices such as input devices (e.g., keyboard, mouse, pen, voice input device, touch input device, etc.) or other peripheral devices (e.g., printer, scanner, etc.) via one or more I/O ports 273. Other conventional I/O devices may be connected as well such as a mouse, keyboard, and so forth. An example communications device 280 includes a network controller 281, which may be arranged to facilitate communications with one or more other computing devices 290, e.g., implant devices such as 100 or medical provider devices as discussed in connection with FIG. 10, over a network communication via one or more communication ports 282.

The communications connection is one example of a communication media. Communication media may typically be embodied by computer readable instructions, data structures, program modules, or other data in a modulated data signal, such as a carrier wave or other transport mechanism, and include any information delivery media. A "modulated data signal" may be a signal that has one or more of its characteristics set or changed in such a manner as to encode information in the signal. By way of example, and not limitation, communication media may include wired media such as a wired network or direct-wired connection, and wireless media such as acoustic, radio frequency (RF), infrared (IR), and other wireless media.

Computing device 200 may be implemented as a portion of a small-form factor portable (or mobile) electronic device such as a cell phone, a personal data assistant (PDA), a personal media player device, a wireless web-watch device, a personal headset device, an application-specific device, or a hybrid device that include any of the above functions. Computing device 200 may also be implemented as a personal computer including both laptop computer and non-laptop computer configurations.

In some embodiments, computing device 200 may support "two-hop" protocol communications between implants, in which a first implant sends (or transmits) via an antenna array implant device data to device 200, which is located external to an organism, and device 200 then forwards the implant device data to a second implant in the organism. This arrangement may be beneficial in some embodiments because tissue is a lossy medium which may hinder direct implant to implant communications.

In some embodiments, computing device 200 may comprise an implant device, microrobot, or other device internal to an organism. Computing device 200 may occasionally be referred to herein as an external device 200, which should not be construed as a requirement that device 200 be located external to an organism in all embodiments. Reference to device 200 as an external device is rather for the purpose of illustrating some non-limiting embodiments.

In some embodiments, device 200 may be configured to communicate with an implant device so that device 200 may securely provide processing, storage and communications assistance to the implant device. Small size is generally advantageous for an implant, while much larger sizes may be used for devices external to the organism. Therefore, device 200 may be equipped to perform data storage and analysis on behalf of an implant, may communicate with other devices on behalf of implant, and may send implant commands to an implant as part of implant device data, as appropriate. Transmissions to and from an implant device may be encrypted or otherwise secured using for example a proprietary wireless communications protocol.

Figure 3:
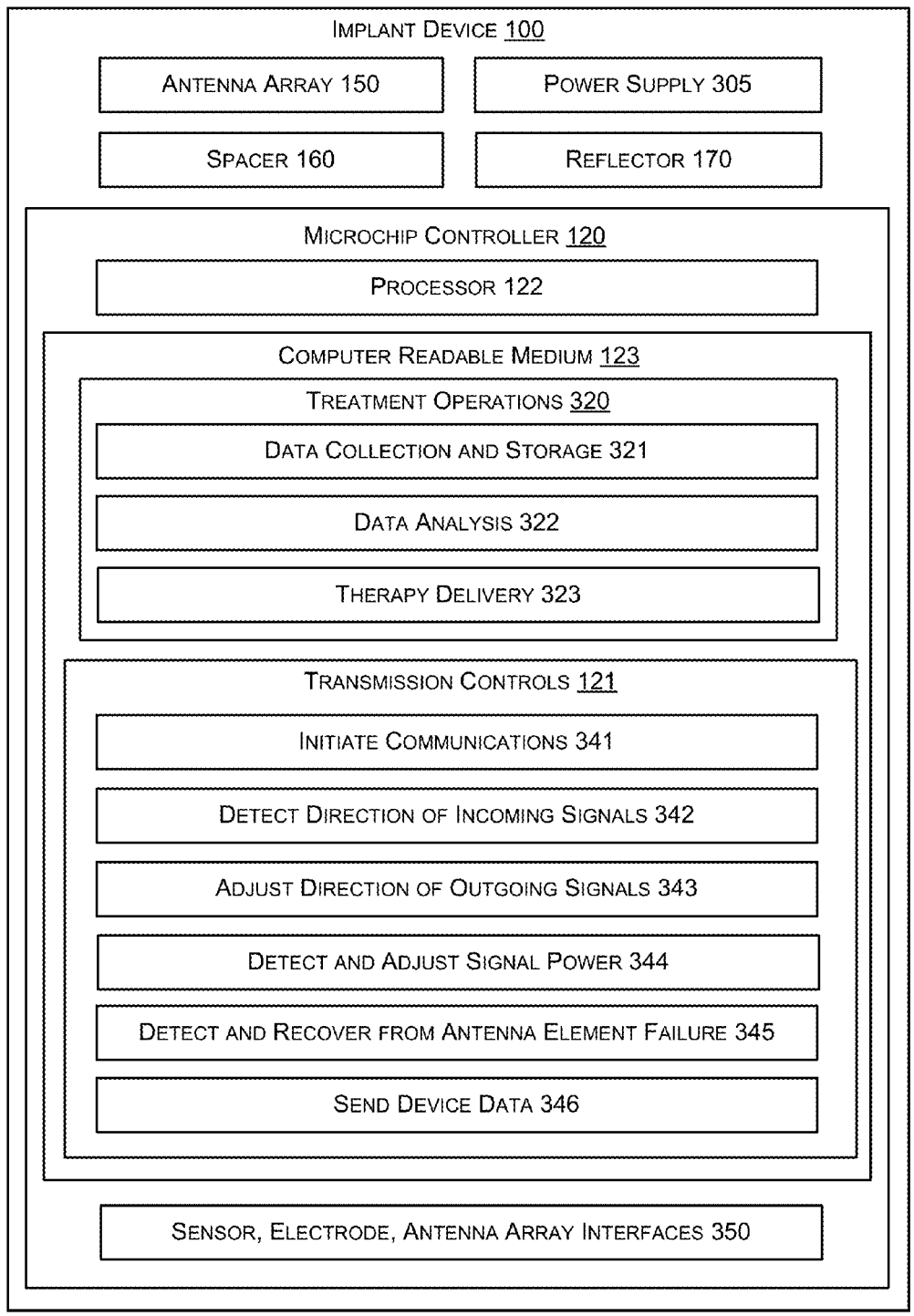
FIG. 3 is a block diagram illustrating additional example aspects of an implant device.

FIG. 3 is a block diagram illustrating additional example aspects of an implant device 100, arranged in accordance with at least some embodiments of the present disclosure. Elements of FIG. 3 introduced in FIG. 1 are assigned like identifiers, including antenna array 150, spacer 160, reflector 170, microchip controller 120, processor 122, computer readable medium 123 and transmission controls 121. Furthermore, implant device 100 may be an electronic device that may contain aspects of a computing device such as the device described with reference to FIG. 2. Implant device 100 may generally comprise a small form factor device in which features and components are miniature and designed for low power consumption.

FIG. 3 may further include power supply 305 and additional aspects of microchip controller 120. In particular, microchip controller 120 may include a variety of modules comprising instructions on computer readable medium 123 which may be executable by processor 122, and microchip controller 120 may include sensor, electrode, and array antenna interfaces 350.

Computer readable medium 123 may include modules for "Treatment Operations" 320 and "Transmission Controls" 121. Treatment operations 320 may include for example "Data Collection And Storage" 321, "Data Analysis" 322, and "Therapy Delivery" 323. Transmission controls 121 may include modules for "Initiate Communications" 341, "Detect Direction of Incoming Signals" 342, "Adjust Direction of Outgoing Signals" 343, "Detect And Adjust Signal Power" 344, "Detect And Recover From Antenna Element Failure" 345, and "Send Device Data" 346.

With reference to FIG. 3, in some embodiments operations of an implant device 100 may be carried out by a microchip controller 120 powered by a power supply 305 such as a battery. The processor 122 may execute instructions recorded on computer readable medium 123. It will be appreciated that implant device 100 is an electronic device, and microchip controller 120 is also an electronic device. Implant device 100, microchip controller 120, and/or any of the various sensors, electrodes, and other components with which the implant device 100 and microchip controller 120 may be equipped may accordingly be referred to herein as an electronic device.

"Treatment Operations" modules 320 may generally comprise modules to perform routine operations of an implant device 100. Treatment Operations modules 320 may include for example "Data Collection And Storage" module 321 to gather biometric data from sensors and storing the biometric data in a memory. Treatment Operations modules 320 may also include for example "Data Analysis" module 322 to analyze biometric data. While data analysis requires power consumption, which may desirably be minimized in many implanted devices. For example, where it may be efficiently determined that certain collected data has a high probability of being irrelevant, it may be more energy-efficient to discard the irrelevant data rather than transmit irrelevant data to an external device for further analysis. Data Analysis module 322 may also comprise data compression instructions in some embodiments. Treatment Operations module 320 may also include for example "Therapy Delivery" module 323 configured to deliver therapies by the implant device 100 to an organism. Therapy Delivery module 323 may include for example instructions to control heartbeat regulation signals of a pacemaker, insulin release of a glucose monitor, electricity discharges of brain electrodes, and/or instructions to control any of the other therapies administratable by an implant device.

"Transmission Controls" modules 121 may generally comprise instructions/modules adapted to control one or more of the timing, initiation, receiving and/or sending of implant device data via an antenna array with properties selected for use with particular embodiments. "Initiate Communications" module 341 may comprise instructions adapted to initiate sending and/or receiving of communications with an external device via an antenna array. In some embodiments, Initiate Communications module 341 may be configured to use a timer to periodically initiate transmissions via the antenna array, for example, periodically transmitting collected device data via the antenna array to an external device. In some embodiments, Initiate Communications module 341 may be configured to respond to a wake-up signal received from an external device via the antenna array. In some embodiments, Initiate Communications module 341 may be configured to respond to detection of an external device within transmission range of the antenna array. In some embodiments, Initiate Communications modules 341 may be arranged to initiate communications by sending an emergency distress signal via the antenna array, in response to detection of a dangerous condition in the organism. Communications may also be initiated in response to non-emergency conditions, such as low battery power remaining in an implant device power supply or failure of a non-essential implant device component such as, in some embodiments, an individual antenna element of the antenna array.

In some embodiments, Transmission Controls module 121 may include "Detect Direction of Incoming Signals" module 342. Because an antenna array contains a plurality of antenna elements, the relative phases of signals arriving at different antenna elements may be analyzed by module 342 to determine direction of the incoming signals.

Figure 8:
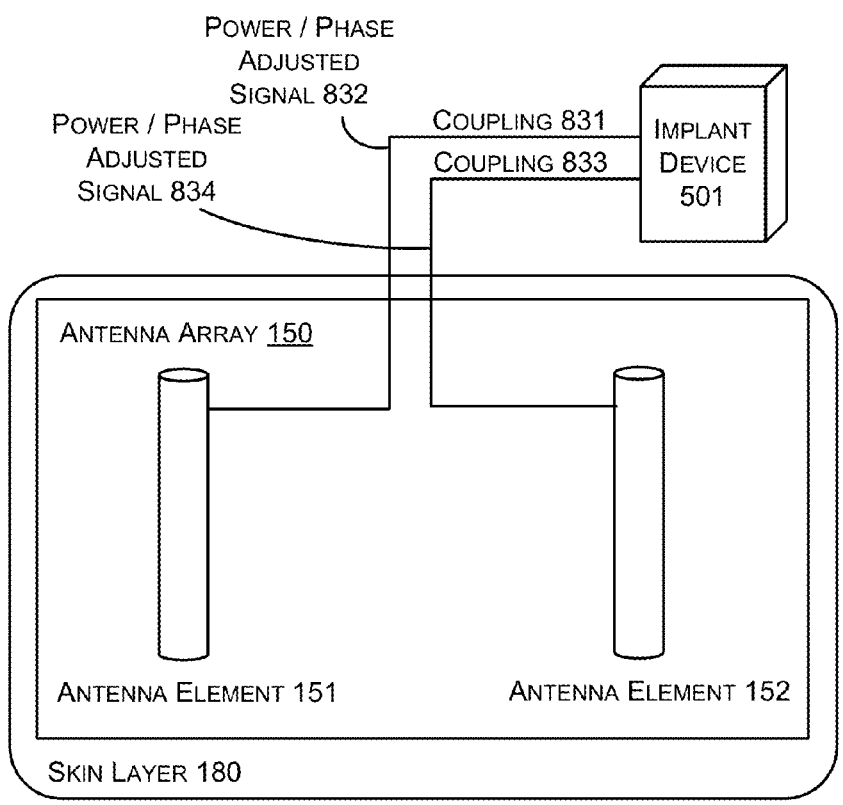
FIG. 8 is a block diagram illustrating an example antenna array unit with separately controllable antenna elements.

In some embodiments, Transmission Controls module 121 may include "Adjust Direction of Outgoing Signals" module 343. Modules 343 may for example be adapted to respond to detection of incoming signal direction by module 342 by sending outgoing signals in a substantially opposite direction. For example, if an external device is transmitting to an implant device 100 from a position thirty degrees off of a vector normal to the tissue plane, the implant device 100 may detect the direction of the external device using module 342, and use module 343 to direct transmitted signals in the opposite direction, i.e., to the detected position of the external device, to improve signal power and transmission quality at the external device. In some embodiments, module 343 may make use of separately controllable antenna elements, for example, as illustrated in FIG. 8. By adjusting the phase of the signals transmitted by the antenna elements, the direction of strongest signal may be correspondingly adjusted. Appropriate controllable circuitry for directing antenna array transmissions, such as by adjusting phase of antenna element signals, may be furthermore used in some embodiments. While direction control may be achieved using phase adjustment of antennas in an antenna array comprising two antenna elements, additional control may be used by adding controllable antenna elements, as appreciated by those of skill in antenna theory.

In some embodiments, Transmission Controls module 121 may include "Detect And Adjust Signal Power" module 344. Detect And Adjust Signal Power module 344 may for example be adapted to detect power of a signal received from an external device, and may be arranged to increase and/or decrease a power of a signal sent to an antenna array based on the detected signal power.

For example, two predetermined signal power thresholds, comprising a low power threshold and a high power threshold, may be predetermined in some embodiments. If a received signal is measured to have a received signal power lower than the low power threshold, the received signal power may be determined to be weak. Where a received signal power is determined to be weak, a transmitted signal power calculated by module 344 may be relatively strong (e.g., at or above the high power threshold), to account for any circumstances producing the weak received signal.

Conversely, where a received signal is measured to have a received signal power higher than the high power threshold, the received signal power may be determined to be strong. Where a received signal power is determined to be strong, a transmitted signal power calculated by module 344 may be relatively weak (e.g., at or below the low power threshold), to preserve implant device battery power under circumstances in which a strong signal may not be necessary.

Detect And Adjust Signal Power module 344 for an antenna array may be different from instructions that would be used for a single antenna, at least in part due to the addition of signals from the multiple antenna elements. Module 344 may be arranged to perform the appropriate adjustment for the properties of particular antenna arrays. Furthermore, embodiments using a reflector may be configured to transmit different signal powers, and respond differently to changes in signal power, as embodiments without a reflector. Signal power calculations made by module 344 may be implemented according to the presence or absence of a reflector as appropriate for particular array antenna and reflector embodiments.

In some embodiments, Transmission controls 121 may include "Detect and Recovering From Antenna Element Failure" module 345. One advantage of using an antenna array may be that implant device transmissions may remain possible even after failure of one of the antenna elements of the array. The remaining non-failed antenna(s) of the array may continue sending and/or receiving device transmissions. In some embodiments, module 345 may respond to circuitry for detecting failure of an antenna element, and may respond to this detected failure. In some embodiments, the response implemented by module 345 may comprise including antenna element failure data in implant device data 132 that may be sent to an external device, so that the failure may be brought to the attention of the implant user or medical personnel. Antenna element failure data may for example identify one or more failed antenna elements, or may provide a percentage of failed or non-failed antenna elements remaining in an antenna array. In some embodiments, the response implemented by module 345 may comprise adjusting signal power using module 344 and/or utilizing modules 342 and 343 to optimize communications with remaining functioning antenna element(s).

In some embodiments, Transmission Controls 121 may include "Send Device Data" module 346. Module 346 may be adapted to encode implant device data 132 into a signal for wireless transmission, and send the signal to an array antenna. The signal may be modulated, amplified, or otherwise adjusted by a variety of antenna array electronics as appropriate for particular embodiments. Module 346 may also be accompanied by instructions for decoding communications received from an external device via the antenna array.

FIG. 3 illustrates sensor, electrode, and antenna array interfaces 350 as may be included in implant device 100. Interfaces 350 may comprise software and/or hardware aspects. For example, interfaces 350 may comprise hardware plug and wire structures and corresponding circuitry for sending and receiving data to and from one or more sensors, electrodes, and/or antenna arrays. Hardware aspects may be accompanied by instructions for microchip controller 120 to convert, read, and/or store received data.

Figure 4:
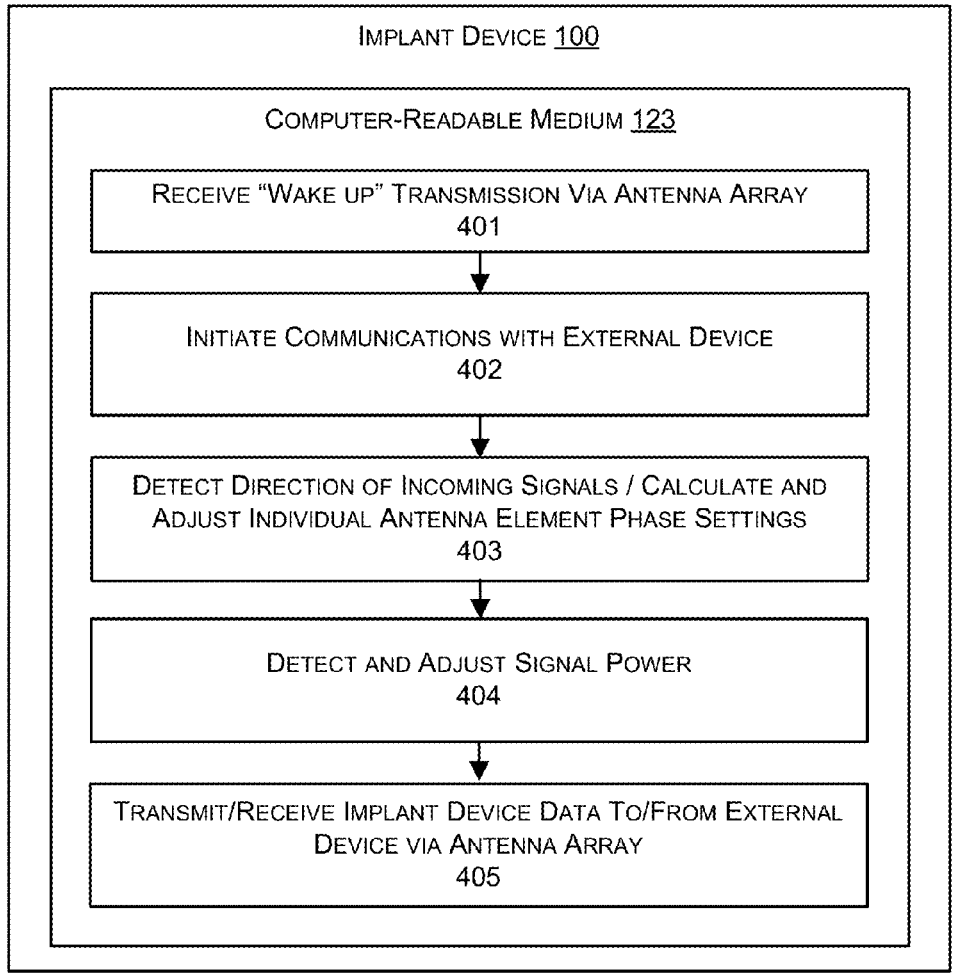
FIG. 4 is a flow diagram illustrating example operations that may be performed by an implant device.

FIG. 4 is a flow diagram illustrating example operations that may be performed by an implant device 100 that is arranged in accordance with at least some embodiments of the present disclosure. The example flow diagram may include one or more operations/modules as illustrated by blocks 401-405, which may represent operations as may be performed in a method, functional modules in an implant device 100, and/or instructions as may be recorded on a computer readable medium 123 to be carried out by the various functional elements illustrated in FIG. 3. The illustrated blocks 401-405 may be arranged to provide functional operations including one or more of "Receive "Wake-Up" Transmission Via Antenna Array" at block 401, "Initiate Communications With External Device" at block 402, "Detect Direction of Incoming Signals / Calculate And Adjust Individual Antenna Phase Settings" at block 403, "Detect And Adjust Signal Power" at block 404, and/or "Transmit/Receive Implant Device Data To/From External Device Via Antenna Array" at block 405.

In FIG. 4, blocks 401-405 are illustrated as being performed sequentially, with block 401 first and block 406 last. It will be appreciated however that these operations may be re-ordered as convenient to suit particular embodiments, and that these blocks or portions thereof may be performed concurrently in some embodiments. It will also be appreciated that in some examples various blocks may be eliminated, divided into additional blocks, and/or combined with other blocks.

FIG. 4 illustrates an example method by which an implant device 100 communicates with an external device. In general, the implant device initiates communications in blocks 401-402, adjust signal settings in blocks 403-404, and/or communicate implant device data in block 405.

In block 401, an implant device 100 may for example receive a low-power "wake-up" transmission via an antenna array coupled to the implant device 100. In some embodiments, implant device 100 may for example comprise a wake-up receiver coupled to an antenna array. The wake-up receiver may comprise a low-noise amplifier and an ultra low power wake up circuit. A communication of a frequency for which the wake-up receiver is designed, e.g., a 2.45 GHz signal, may cause the wake-up receiver to signal a microchip controller to start a communication session between implant device 100 and an external device. Block 401 may be followed by block 402.

In block 402, signals may be sent to and/or received from the external device by the implant device 100 via an antenna array. In some embodiments, the signals may comprise test signals that may be measured for the purpose of making signal adjustments in blocks 403 and 404. In some embodiments, the signals may comprise an initial handshake for initiating a communication session. In some embodiments, the signals may comprise a first set of implant device data that is transmitted by the implant device 100, received by the implant device 100, or both. In some embodiments, instructions such as instructions associated with module 341 from FIG. 3 may be executed by a microchip controller to initiate communications pursuant to block 402. Block 402 may be followed by block 403.

In block 403, components such as modules 342 and 343 from FIG. 3 may be activated to tune antenna array transmission direction, as described above. In some embodiments, block 403 may accommodate a position of an external device by directing a strongest signal in a direction of the external device. Any number of other factors may also affect optimal transmission direction. For example, clothes worn by a person in which the implant is installed, tissue layers of varying thickness and chemical composition, and electromagnetic interference environment may all impact optimal transmission direction. In some embodiments, optimal transmission direction may be calculated by an external device to leverage the typically high processing power and power supply of the external device. Transmission direction control instructions may then be sent by the external device, and received at the implant device 100. The implant may modify transmission direction of an array antenna according to the received transmission direction control instructions. Block 403 may be followed by block 404.

In block 404, components such as module 344 from FIG. 3 may be activated to adjust signal power, as described above. In some embodiments, signal power may be adjusted based on a strength of received transmission signals, e.g., with an inverse relationship to the strength of received signals as described above. In some embodiments, signal power may be adjusted based on what type of device the implant device 100 is communicating with. For example, direct communication with another implant device may utilize more signal power than communication with another implant device via an external device, using a so-called "two-hop" protocol. In some embodiments, a type of antenna array and/or specific antenna array properties may be accounted for in adjusting signal power. For example, the presence of a reflector, number of antenna elements, phase settings of antenna elements, and other antenna array properties may be accounted for in power adjustment calculations. Block 404 may be followed by block 405.

In block 405, implant device data may be sent to and received from an external device. In general, this operation may comprise preparing data for wireless transmission pursuant to a selected wireless transmission protocol, for example by preparing appropriate discrete data packets, transmission start packets, transmission checksum packets, transmission acknowledgement packets, and transmission end packets. A carrier wave of an appropriate transmission frequency, e.g., a carrier wave in the 400 MHz range as presently specified by MICS, may then be modulated to encode the prepared data packets. In some embodiments, a carrier wave for transmission by an antenna array may be split, so that each element of the antenna array transmits an identical signal. In some embodiments, carrier waves for transmission by one or more antenna elements may furthermore be delayed in order to adjust the relative phases of the antenna elements, e.g., in order to achieve signal direction adjustment as described above.

Figure 5:
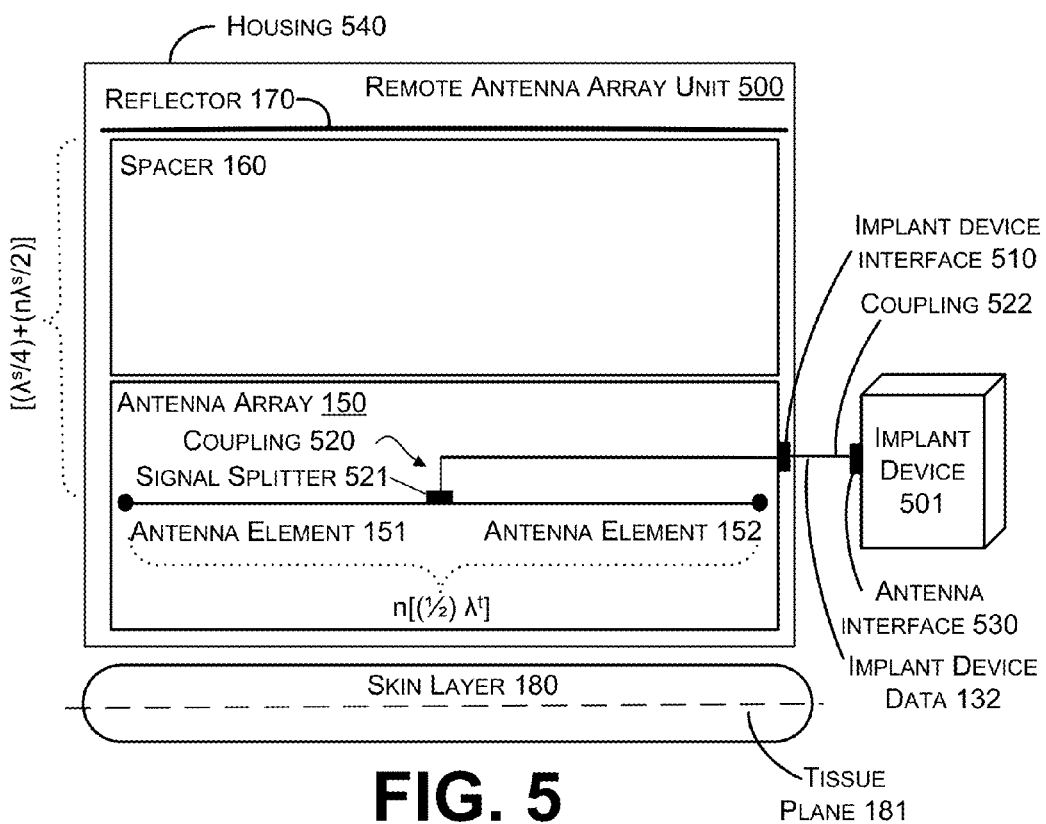
FIG. 5 is a block diagram illustrating an example remote antenna array unit coupled to an implant device.

FIG. 5 is a block diagram illustrating an example remote antenna array unit 500 coupled to an implant device 501, arranged in accordance with at least some embodiments of the present disclosure. Remote antenna array unit 500 may be disposed under a tissue layer such as skin layer 180. A tissue plane 181 associated with skin layer 180 is also illustrated. Remote antenna array unit 500 may comprise one or more of a housing 540, a reflector 170, a spacer 160, an antenna array 150, and/or an implant device interface 510. Antenna array 150 may comprise two or more antenna elements such as antenna elements 151 and 152. As with the housing 110 of FIG. 1, the housing 540 of the remote antenna array unit 500 and/or antenna elements 151 and 152 may be oriented so that the remote antenna array unit 500 and antenna elements 151 and 152 may be substantially parallel to the tissue plane 181.

Within the remote antenna array unit 500, antenna elements 151 and 152 may be coupled to implant device interface 510 via a coupling 520 which may comprise a signal splitter 521 junction with equal length wire leads to each of the antenna elements 151 and 152. Implant device interface 510 may be coupled to an antenna interface 530 associated with implant device 100 via wired or wireless connection 532. Implant device data 132 may be communicated between implant device 501, antenna array 150, and/or the antenna elements 151 and 152 thereof, via couplings 520 and 522, interfaces 510 and 530, and signal splitter 521.

Embodiments such as illustrated in FIG. 5 allow coupling an implant device 510 at an optimal treatment location, while placing the antenna array unit 500 at an optimal location for wireless transmissions, such as just underneath the skin 180. Couplings 520 and 522 may comprise a signal splitter 521, as illustrated, or may implement individual couplings as illustrated in FIG. 8, allowing the implant device 501 to support signal direction detection and transmission direction control of remote antenna array unit 500, as described above. The signal splitter 521 may for example include a first port and a second port, wherein the first port and the second port are coupled to a respective one of the two or more individual antenna elements 151, 152, and wherein the signal splitter is configured such that electromagnetic waves associated with the first and second ports are in phase with one another.

In some embodiments, remote antenna array unit 500 may furthermore comprise an individual power supply and microchip controller (not shown) allowing for signal power modulation, direction detection and direction control by the remote antenna array unit 500. Embodiments including an individual power supply and microchip controller at the array unit also allow the option of wireless communications with implant device 501, for example, implementing a two-hop wireless protocol in which transmission from device 501 are relayed by remote antenna array unit 500 to an external device or to another implant device. Such other implant device may be coupled to remote antenna array unit 500 via a wired or wireless connection, just as with implant device 501.

FIG. 5 illustrates example selected positions of antenna elements 151 and 152 and reflector 170. Antenna elements 151 and 152 may for example be disposed at a distance of $n[(\frac{1}{2})\lambda^r]$, where n comprises the set of positive whole numbers [1, 2, 3, . . . ], and $[(\frac{1}{2})\lambda^r]$ is one half the wavelength of an electromagnetic wave emitted by an antenna element, adjusted for the dielectric constant of the tissue (as denoted by the letter t). By positioning the antenna elements at a fixed distance of $n[(½)\mu^r]$ apart, the fixed distance may be selected to promote destructive interference of electromagnetic waves emitted by the individual antenna elements in the plane of the tissue layer 181, and constructive interference of the electromagnetic waves in a direction substantially normal to the plane of the tissue layer. Some variations from the one-half wavelength spacing formula given here may also promote destructive interference in the tissue plane, so long as the variation remains generally within a range of ±¼ wavelength, as will be appreciated.

FIG. 5 illustrates a distance of $[(\lambda^s/4)+(n\lambda^s/2)]$ between the plane of antenna elements 151 and 152 and the reflector 170, where n comprises the set of positive whole numbers [0, 1, 2, 3, . . . ], and $¼\lambda^s$ is one fourth the wavelength of an electromagnetic wave emitted by an antenna element, adjusted for the dielectric constant of the spacer material (as denoted by the letter s), and $n\lambda^s/2$ is n times one half the wavelength of an electromagnetic wave emitted by an antenna element, adjusted for the dielectric constant of the spacer material (again, as denoted by the letter s). The antenna array 150 and reflector 170 may for example be configured as an image antenna. By positioning the reflector 170 at a fixed reflecting distance of $[(\lambda^s/4)+(n\lambda^s/2)]$, the reflecting distance is selected to promote constructive interference of reflected electromagnetic waves with the electromagnetic waves emitted by the individual antenna elements in a direction substantially normal to the plane of the tissue layer. This is because the reflector 170 causes a phase inversion, or one-half wavelength (180°) phase shift. A round trip of $2[(\lambda^s/4)+(n\lambda^s/2)]$ plus a one-half wavelength phase shift will cause reflected electromagnetic waves to be in-phase with waves emitted substantially normal to the tissue plane 181.

In some embodiments comprising a reflector 170, signal modulation may be adjusted to prevent negative interference effects of modulated signals. This adjustment may comprise for example modulating transmitted electromagnetic waves in half wavelength segments, and leaving every other half-wavelength unmodulated. Using this approach, the unmodulated reflected wave may boost signal power of the modulated unreflected wave, without negatively interfering with modulated wave aspects. Transmission time doubles using this approach, however transmission power also doubles. The transmission time vs. transmission power tradeoff may be worthwhile in some embodiments, in particular where thick layers of tissue dispose a lossy medium transmission barrier between the antenna array and external device.

Figure 6:
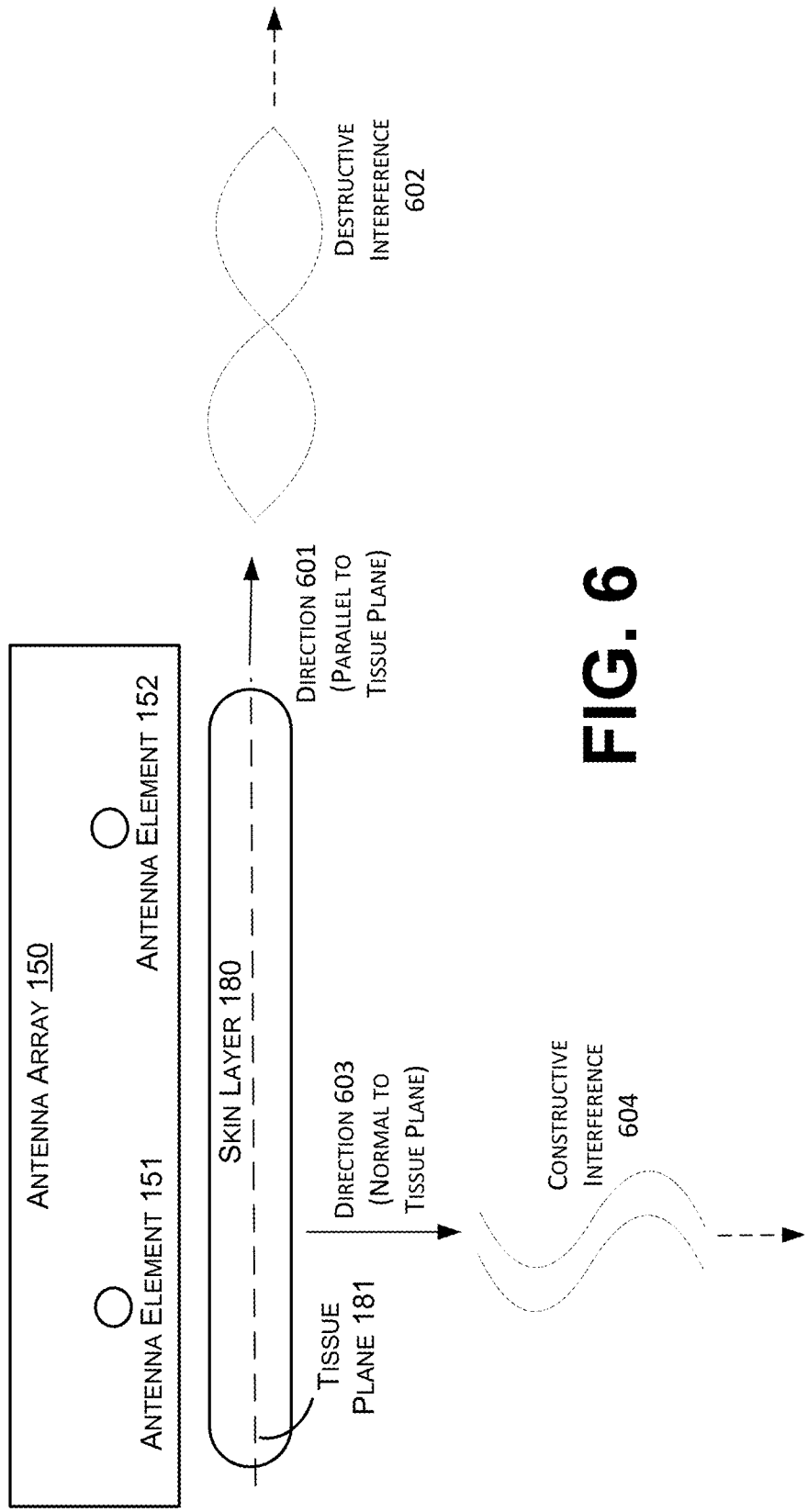
FIG. 6 is a diagram illustrating example electromagnetic waves substantially parallel and normal to a tissue plane.

FIG. 6 is a diagram illustrating example electromagnetic waves substantially parallel and normal to a first plane, in accordance with at least some embodiments of the present disclosure. Here, the first plane is also a plane of a tissue layer, and so is referred to as a tissue plane 181. FIG. 6 illustrates an antenna array 150 comprising antenna elements 151 and 152. The antenna array 150 may be disposed over skin layer 180, and substantially parallel to tissue plane 181. Electromagnetic waves travelling in a direction 603 substantially normal to tissue plane 181 may produce constructive interference 604. Electromagnetic waves travelling in a direction 601 parallel to tissue plane 181 may produce destructive interference 602.

Figure 7:
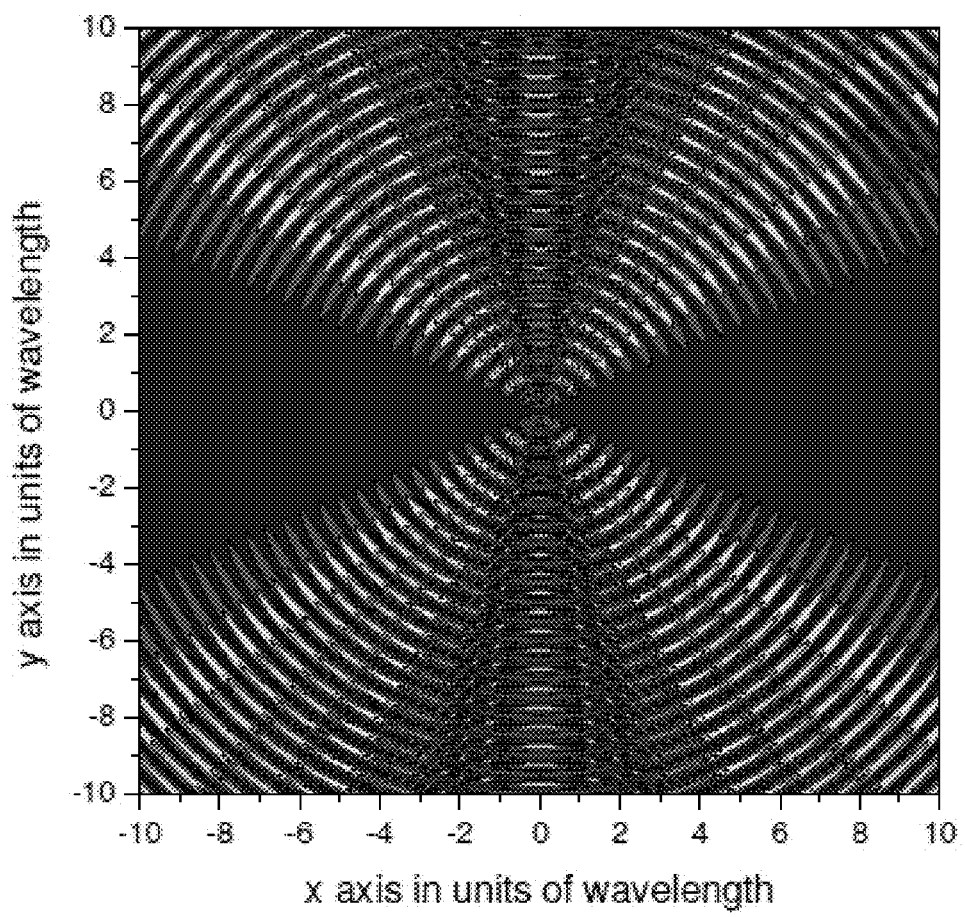
FIG. 7 is a graph illustrating an example electromagnetic interference pattern from an antenna array comprising two dipole antennas.

FIG. 7 is a graph illustrating an example electromagnetic interference pattern from an antenna array comprising two dipole antennas, arranged in accordance with at least some embodiments of the present disclosure. In FIG. 7, the antenna array is positioned in the center of the graph. Destructive interference produces little or no radiation in the left and right middle zones of the graph. The strongest signal is centered over the vertical line in the center of the graph, passing through the zero on the horizontal axis. Signal strength then tapers off in the zones to the left and right of the strongest signal.

In FIG. 7, if the horizontal line passing through the zero on the vertical axis were a line on a tissue plane, there would be substantially zero radiation in the tissue plane. Radiation would instead be directed into the organism and away from the organism. The radiation directed into the organism may be reflected using a reflector as disclosed herein (not shown in FIG. 7), thereby enhancing signal strength directed away from the organism and reducing radiation directed into the organism.

FIG. 8 is a block diagram illustrating an example antenna array unit with separately controllable antenna elements, in accordance with at least some embodiments of the present disclosure. FIG. 8 comprises an implant device 501 and a top view of an antenna array 150. Antenna array 150 comprises antenna elements 151 and 152, also shown in top view. Antenna array 150 may be disposed underneath a skin layer 180.

Implant device 501 may be coupled to antenna element 151 via coupling 831, and may thereby send a separately controlled power and/or phase adjusted signal 832. Implant device 501 may be separately coupled to antenna element 152 via coupling 833, and may thereby send a separately controlled power and/or phase adjusted signal 834. Signals 832 and 834 may be encoded with implant device data 132 as described above.

Figure 9:
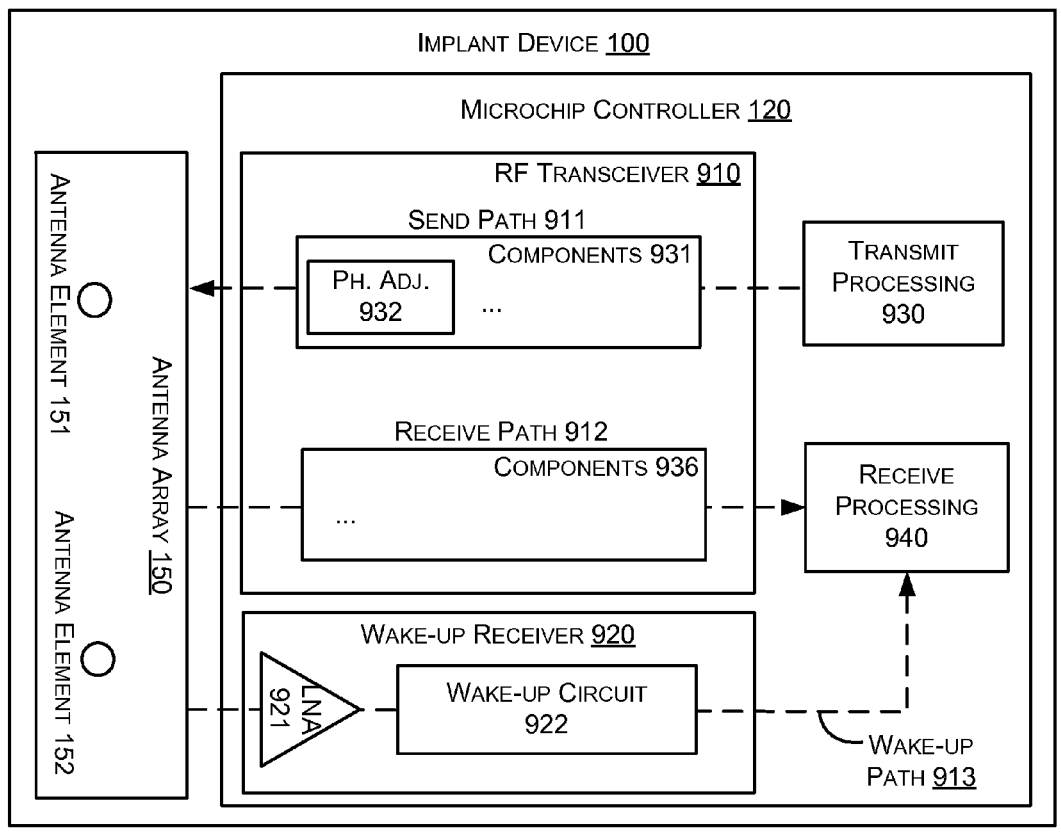
FIG. 9 is a block diagram illustrating an example implant device.

FIG. 9 is a block diagram illustrating an example implant device 100 arranged in accordance with at least some embodiments of the present disclosure. Example implant device 100 comprises microchip controller 120 and antenna array 150. Antenna array 150 may comprise two or more antenna elements 151 and 152. Microchip controller 120 may comprise Radio Frequency (RF) transceiver 910, wake-up receiver 920, transmit processing 930 and/or receive processing 940. Wake-up receiver 920 may comprise low-noise amplifier (LNA) 921 and/or wake-up circuit 922.

In FIG. 9, a dotted arrow from transmit processing 930, through RF transceiver 910, to antenna array 150 indicates a send signal path 911. A dotted arrow from antenna array 150, through RF transceiver 910, to receive processing 940 indicates a receive signal path 912. A dotted arrow from antenna array 150, through wake-up circuit 920, to receive processing 940 indicates a wake-up signal path 913.

FIG. 9 illustrates an implant device 100 comprising a microchip controller 120 with onboard transceiver circuitry 910 and 920 configured for interaction with antenna array 150 as well as transmit processing 930 and receive processing 940. It should be appreciated that RF transceiver 910 and wake-up receiver 920 may be moved to an off-chip or other external location from micro-chip controller 120 in some embodiments.

In FIG. 9, the RF transceiver 910 may comprise one or more of amplifiers, filters, phase adjusters, Intermediate Frequency (IF) modulators, demodulators Analog-to-Digital (A/D) converters, and/or Digital-to-Analog (D/A) converters, as appropriate for particular embodiments. For example, in some embodiments send signal path 911 may comprise components 931 such as one or more of a D/A converter, an IF modulation component, a phase adjuster 932, and/or an amplifier. Implant device data to be sent via send signal path 911 may be initially prepared by transmit processing 930, then sent to RF transceiver 910 to be sent via the various components 931 thereof along send signal path 911 for transmission to an external device. Antenna array 150 may for example send the implant device data using a MICS frequency ranges specified by the FCC and/or the ETSI.

In some embodiments, receive signal path 912 may comprise components 936 such as one or more of an amplifier, a phase adjuster, a demodulator, and/or an (A/D) converter. Implant device data may be received at antenna array 150 on a signal in a MICS frequency range specified by the FCC and/or the ETSI. Implant device data may be processed by RF transceiver 910 via the various components 936 along receive signal path 912, then passed to receive processing 940.

In some embodiments, wake-up signal path 913 may comprise one or more of a LNA and/or a wake-up circuit, as shown. A wake-up signal comprising a signal of a predetermined frequency may be received at antenna array 150, processed by the various components along wake-up signal path 913, generating a wake-up signal for the chip 920. Wake up signal path 913 is illustrated as terminating at receive processing 940 however wake-up signal path 913 may terminate at any appropriate control logic for activating the implant device 100 in response to a wake-up signal (not shown) received via antenna array 150.

The above described example in FIG. 9 is not intended to be limiting, and numerous other examples are contemplated. For example, in some example embodiments, the RF transceiver 910 may be implemented as a separate receiver and transmitter. The transceiver may be external to the microchip controller 120 or internal to the microchip controller depending on the particular embodiment. Likewise, for implementations that utilized a separate receiver and transmitter, the receiver and transmitter may be external to the microchip controller 120 or internal to the microchip controller 120. The wake-up receiver 920 may also be either external or internal to the microchip controller 120, as may be required in a particular implementation. Also, the antenna array 150 may either be internal to the implant device 100 or external to the implant device 100, as may be required in a particular implementation.

Figure 10:
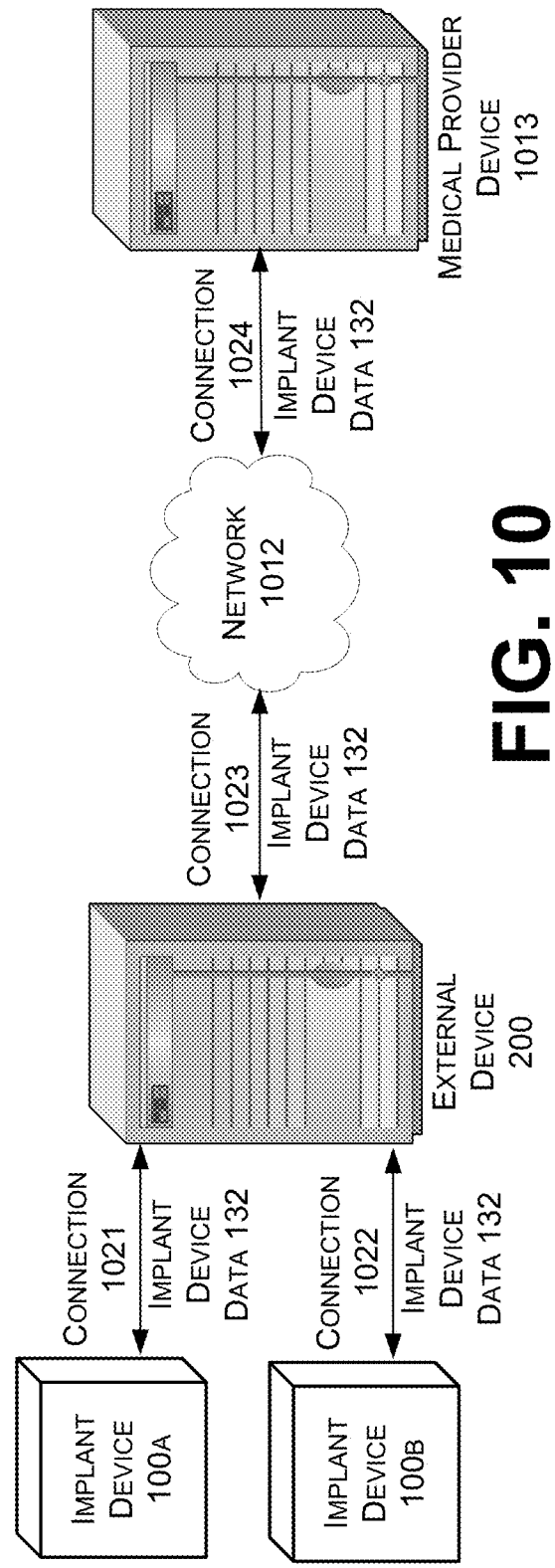
FIG. 10 is a diagram illustrating example implant devices, an external device, a network and a medical provider device; all arranged in accordance with at least some embodiments of the present disclosure.

FIG. 10 is a diagram illustrating example implant device(s) 100A and 100B, an external device 200, a network 1012, and a medical provider device 1013, arranged in accordance with at least some embodiments of the present disclosure. Implant devices 100A and 100B may be coupled to external device 200 via wireless connections 1021 and 1022, respectively, along which implant device data 132 may be communicated. External device 200 may be coupled to network 1012 via wired or wireless connection 1023, along which implant device data 132 may be communicated. Network 1012 may be coupled to medical provider device 1013 via wired or wireless connection 1024, along which implant device data 132 may be communicated.

FIG. 10 illustrates example implant devices 100A and 100B in a system comprising a variety of other devices, arranged in accordance with at least some embodiments of the present disclosure. Implant device data 132 may be sent from an implant device 100A, via an array antenna as shown in FIG. 1, FIG. 5 and FIG. 8, to an external device 200. In some embodiments, external device 200 may for example implement a two-hop protocol in which external device 200 is adapted to forward implant device data 132 to implant device 100B. In some embodiments, external device 200 may be arranged to issue commands to one or more implant devices, for example, commands concerning delivery of therapies by the implants. In some embodiments, external device 200 may be configured to store implant device data 132, which may be retrieved at medical provider device 1013 for example during a patient visit to a medical provider. In some embodiments, external device 200 may be configured to communicate certain implant device data 132 to medical provider device 1013 via network 1012. For example, a patient emergency alert may be sent to medical provider device 1013 if necessary.

There is little distinction left between hardware and software implementations of aspects of systems; the use of hardware or software is generally (but not always, in that in certain contexts the choice between hardware and software may become significant) a design choice representing cost vs. efficiency tradeoffs. There are various vehicles by which processes and/or systems and/or other technologies described herein may be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; if flexibility is paramount, the implementer may opt for a mainly software implementation; or, yet again alternatively, the implementer may opt for some combination of hardware, software, and/or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples may be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, may be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link, etc.).

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein may be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems. The herein described subject matter sometimes illustrates different components contained within, or connected with, different other components. It is to be understood that such depicted architectures are merely examples, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality may be seen as "associated with" each other such that the desired functionality is achieved, irrespective of architectures or intermediate components. Likewise, any two components so associated may also be viewed as being "operably connected", or "operably coupled", to each other to achieve the desired functionality, and any two components capable of being so associated may also be viewed as being "operably couplable", to each other to achieve the desired functionality. Specific examples of operably couplable include but are not limited to physically connectable and/or physically interacting components and/or wirelessly interactable and/or wirelessly interacting components and/or logically interacting and/or logically interactable components.

With respect to the use of substantially any plural and/or singular terms herein, those having skill in the art may translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

While certain example techniques have been described and shown herein using various methods, devices and systems, it should be understood by those skilled in the art that various other modifications may be made, and equivalents may be substituted, without departing from claimed subject matter. Additionally, many modifications may be made to adapt a particular situation to the teachings of claimed subject matter without departing from the central concept described herein. Therefore, it is intended that claimed subject matter not be limited to the particular examples disclosed, but that such claimed subject matter also may include all implementations falling within the scope of the appended claims, and equivalents thereof.

The invention claimed is:

1. A microchip controller adapted to be coupled with an implant device that is implantable inside an organism and wherein the microchip controller is adapted to be coupled with an implant device antenna array to wirelessly communicate with a device external to the implant device, the antenna array comprising two or more individual antenna elements, the microchip controller comprising:
   a Radio Frequency (RF) transceiver that includes electronic circuit components that implement an RF transceiver send path, wherein the electronic circuit components that implement the RF transceiver send path comprise at least one phase adjuster, and electronic circuit components that implement an RF transceiver receive path;
   wherein the RF transceiver send path is configured to convert implant device data into RF signals, and to transmit RF signals via the antenna array to the device external to the implant device, and wherein the RF transceiver receive path is configured to convert RF signals received at the antenna array into data adapted for consumption by the implant device;
   wherein the microchip controller is adapted to evaluate relative phases of RF signals received via the individual antenna elements of the antenna array to determine a transmission direction of RF signals received at the antenna array;

wherein the microchip controller is configured to control the RF transceiver send path comprising at least one phase adjuster to adjust phase of RF signals transmitted by each of the individual antenna elements in the antenna array to thereby adjust a strongest signal direction of transmitted RF signals such that the strongest signal direction of the transmitted RF signals is in the direction of the RF signals received at the antenna array.

2. The microchip controller of claim 1, wherein the RF transceiver send path is adapted for wireless communication in a Medical Implanted Communication Service (MICS) frequency range.

3. The microchip controller of claim 1, further comprising a wake-up receiver configured to receive a wake-up signal from the antenna array and wake up the microchip controller in response to receiving the wake-up signal.

4. The microchip controller of claim 1, wherein the microchip controller is configured to control the RF transceiver send path to adjust phase of RF signals transmitted by each of the individual antenna elements in the antenna array to promote destructive interference of RF signals emitted by the individual antenna elements in a first plane, the first plane corresponding to a tissue plane when the implant device is implanted in the organism, and to promote constructive interference of the RF signals in a direction substantially normal to the first plane.

5. The microchip controller of claim 4, wherein the individual antenna elements of the antenna array are configured in a substantially parallel alignment at a fixed distance with respect to one another of substantially $n[(½)\lambda^t]$, where n comprises a whole number selected from a set of positive whole numbers [1, 2, 3, . . . ], and $[(½)\lambda^t]$ is one half of a wavelength of $\lambda^t$ of RF signals transmitted by the antenna array in tissue inside the organism.

6. The microchip controller of claim 1, wherein the antenna array further comprises a reflector and a spacer material separating the reflector and the antenna array, wherein the reflector is configured at a fixed reflecting distance with respect to the antenna array of $[(\lambda^s/4)+(n\lambda^s/2)]$, where n comprises a whole number selected from a set of positive whole numbers [1, 2, 3, . . . ] and $\lambda^s$ is a wavelength of RF signals transmitted by the antenna array in the spacer material, and wherein the RF transceiver send path is configured to accommodate effects of the reflector on transmitted RF signals when adjusting RF signals transmitted by each of the individual antenna elements in the antenna array.

7. The microchip controller of claim 1, further comprising a signal power control component adapted to control signal level for each of the individual antenna elements, and wherein the microchip controller is configured to adjust an antenna signal level for a non-failed antenna element in response to a detected failure of an individual antenna element.

8. The microchip controller of claim 7, further comprising an antenna element failure detection component adapted to detect the failure of an individual antenna element.

9. The microchip controller of claim 1, wherein the microchip controller is adapted to receive biometric data from one or more sensors, and to include the received biometric data in transmitted implant device data.

10. The microchip controller of claim 1, wherein the microchip controller is adapted to control therapy delivery by the implant device according to instructions received via the RF transceiver receive path.

11. The microchip controller of claim 1, wherein the microchip controller is adapted to initiate a communication via the RF transceiver send path in response to one or more of a low battery event indicating low battery power remaining in the implant device, an emergency condition event associated with a dangerous condition in the organism, or a component failure event indicating failure of an implant device component or individual antenna element.

12. The microchip controller of claim 1, wherein the microchip controller is adapted to adjust signal power of RF signals provided to the antenna array via the RF transceiver send path.

13. The microchip controller of claim 1, wherein the microchip controller is adapted to increase signal power of RF signals provided to the antenna array via the RF transceiver send path when the RF signals received at the antenna array are at or below a low signal power threshold.

14. The microchip controller of claim 1, wherein the microchip controller is adapted to decrease signal power of RF signals provided to the antenna array via the RF transceiver send path when the RF signals received at the antenna array are at or above a high signal power threshold.

15. A wireless communications method for a microchip controller couplable to an implant device that is implantable inside an organism and adapted to wirelessly communicate via an antenna array with a device external to the implant device, the antenna array comprising two or more individual antenna elements, the wireless communications method comprising:
    evaluating relative phases of signals received via the individual antenna elements of the antenna array to determine a transmission direction of the received signals; and
    adjusting phase of the individual antenna elements to transmit a strongest signal in the transmission direction of the received signals, wherein adjusting phase of the individual antenna elements comprises controlling a Radio Frequency (RF) transceiver in the microchip controller;
    wherein the RF transceiver includes electronic circuit components that implement an RF transceiver send path, wherein the electronic circuit components that implement the RF transceiver send path comprise at least a phase adjuster, wherein the microchip controller adjusts the phase adjuster to adjust relative phases of RF signals transmitted by each of the individual antenna elements in the antenna array to thereby adjust the strongest signal direction of transmitted RF signals, and wherein the RF transceiver send path is configured to convert implant device data into RF signals, and to transmit RF signals via the antenna array to the device external to the implant device; and
    wherein the RF transceiver includes electronic circuit components that implement an RF transceiver receive path, and wherein the RF transceiver receive path is configured to convert RF signals received at the antenna array into data adapted for consumption by the implant device.

16. The wireless communications method of claim 15, wherein the RF transceiver send path is adapted for wireless communication in a Medical Implanted Communication Service (MICS) frequency range.

17. The wireless communications method of claim 15, further comprising receiving a wake-up signal from the antenna array and waking up the microchip controller in response to receiving the wake-up signal.

18. The wireless communications method of claim 15, wherein the microchip controller controls the RF transceiver to adjust RF signals transmitted by each of the individual antenna elements in the antenna array to promote destructive interference of RF signals emitted by the individual antenna elements in a first plane, the first plane corresponding to a tissue plane when the implant device is implanted in the organism, and to promote constructive interference of the RF signals in a direction substantially normal to the first plane.

19. The wireless communications method of claim 18, wherein the individual antenna elements of the antenna array are configured in a substantially parallel alignment at a fixed distance with respect to one another of substantially $n[(\frac{1}{2})\lambda^t]$, where n comprises a whole number selected from a set of positive whole numbers [1, 2, 3, . . . ], and $[(\frac{1}{2})\lambda^t]$ is one half of a wavelength $\lambda^t$ of RF signals transmitted by the antenna array in tissue inside the organism.

20. The wireless communications method of claim 15, wherein the antenna array further comprises a reflector and a spacer material separating the reflector and the antenna array, wherein the reflector is configured at a fixed reflecting distance with respect to the antenna array of $[(\lambda^s/4)+(n\lambda^s/2)]$, where n comprises a whole number selected from a set of positive whole numbers [1, 2, 3, . . . ] and $\lambda^s$ is a wavelength of RF signals transmitted by the antenna array in the spacer material, and wherein the RF transceiver send path is configured to accommodate effects of the reflector on transmitted RF signals when adjusting RF signals transmitted by each of the individual antenna elements in the antenna array.

21. The wireless communications method of claim 15, further comprising adjusting signal level for a non-failed antenna element in response to a detected failure of an individual antenna element.

22. The wireless communications method of claim 15, further comprising one or more of:
  receiving biometric data from one or more sensors, and including the received biometric data in transmitted implant device data; or
  controlling therapy delivery by the implant device according to instructions received via the RF transceiver receive path.

23. The wireless communications method of claim 15, further comprising one or more of:
  increasing signal power of RF signals provided to the antenna array via the RF transceiver send path in response to receiving RF signals via the RF transceiver send path, wherein the received RF signals are at or below a low signal power threshold; or
  decreasing signal power of RF signals provided to the antenna array via the RF transceiver send path in response to receiving RF signals via the RF transceiver send path, wherein the received RF signals are at or above a high signal power threshold.

24. A microchip controller adapted to be coupled with an implant device that is implantable inside an organism, wherein the microchip controller is adapted to be coupled with an implant device antenna array to wirelessly communicate with a device external to the implant device, the antenna array comprising two or more individual antenna elements, a reflector and a spacer material separating the reflector and the antenna elements, wherein the reflector is configured at a fixed reflecting distance with respect to the antenna elements of $[(\lambda^s/4)+(n\lambda^s/2)]$, where n comprises a whole number selected from a set of positive whole numbers [1, 2, 3, . . . ] and $\lambda^s$ is a wavelength of Radio Frequency (RF) electromagnetic signals transmitted by the antenna elements in the spacer material, the microchip controller comprising:
  an RF transceiver comprising:
    electronic circuit components that implement an RF transceiver send path, wherein the electronic circuit components that implement the RF transceiver send path comprise at least a phase adjuster; and
    electronic circuit components that implement an RF transceiver receive path;
  wherein the RF transceiver send path is configured to convert implant device data into RF signals, and to transmit RF signals via the antenna array to the device external to the implant device, and wherein the RF transceiver receive path is configured to convert RF signals received at the antenna array into data adapted for consumption by the implant device;
  wherein the microchip controller is configured to control the RF transceiver send path to adjust phase of RF signals transmitted by each of the individual antenna elements in the antenna array to thereby adjust a strongest signal direction of transmitted RF signals; and
  wherein the microchip controller is configured to accommodate effects of the reflector on transmitted RF signals when adjusting RF signals transmitted by each of the individual antenna elements in the antenna array.

25. The microchip controller of claim 24, wherein the microchip controller is configured to control the RF transceiver send path to adjust phase of RF signals transmitted by each of the individual antenna elements in the antenna array to promote destructive interference of RF signals emitted by the individual antenna elements in a first plane, the first plane corresponding to a tissue plane when the implant device is implanted in the organism, and to promote constructive interference of the RF signals in a direction substantially normal to the first plane.

26. The microchip controller of claim 24, wherein the microchip controller is adapted to adjust signal power of RF signals provided to the antenna array via the RF transceiver send path.

27. The microchip controller of claim 26, wherein the microchip controller is adapted to adjust signal power of RF signals provided to the antenna array via the RF transceiver send path responsive to signal power of RF signals received via the RF transceiver receive path.

* * * * *

UNITED STATES PATENT AND TRADEMARK OFFICE
CERTIFICATE OF CORRECTION

Page 1 of 1

PATENT NO. : 9,002,456 B2
APPLICATION NO. : 13/785861
DATED : April 7, 2015
INVENTOR(S) : Goossen It is certified that error appears in the above-identified patent and that said Letters Patent is hereby corrected as shown below:

On the Title Page, Item "(72)", under "Inventor", in Column 1, Line 1, delete "Keith W Goossen," and insert -- Keith W. Goossen, --, therefor.

On Page 2, Item "(56)", References Cited under "OTHER PUBLICATIONS", in Column 1, Lines 4-5, delete "Eldosoky, The role of the skin layer in the communication between the implanted sensors and the outside controller, undated, 4 pages.".

In the specification

In Column 1, Lines 7-8, delete "claimed to" and insert -- claimed under 35 U.S.C. § 121 to --, therefor.

In Column 1, Line 9, delete "and which" and insert -- which --, therefor.

In Column 6, Line 24, delete "AN ports 263." and insert -- A/V ports 263. --, therefor.

In Column 16, Line 44, delete "and or" and insert -- and/or --, therefor.

In the claims

In Column 22, Line 4, in Claim 24, delete "[($\lambda^{s/}4$)+($n\lambda^{s/}2$)]," and insert -- [($\lambda^{s}/4$)+($n\lambda^{s}/2$)], --, therefor.

Signed and Sealed this
Tenth Day of November, 2015

Michelle K. Lee
*Director of the United States Patent and Trademark Office*